(12) United States Patent
Sawusch

(10) Patent No.: US 6,171,336 B1
(45) Date of Patent: Jan. 9, 2001

(54) METHOD, IMPLANT, AND APPARATUS FOR REFRACTIVE KERATOPLASTY

(76) Inventor: Mark R. Sawusch, 4487 Colbath Ave., Sherman Oaks, CA (US) 91423

( * ) Notice: Under 35 U.S.C. 154(b), the term of this patent shall be extended for 0 days.

(21) Appl. No.: 08/823,149

(22) Filed: Mar. 25, 1997

Related U.S. Application Data

(60) Provisional application No. 60/014,169, filed on Mar. 26, 1996.

(51) Int. Cl.$^7$ ........................................................ A61F 2/14
(52) U.S. Cl. .............................. 623/5.11; 128/898; 606/5
(58) Field of Search ............................. 623/5.11; 606/5; 128/898

(56) References Cited

U.S. PATENT DOCUMENTS

| | | |
|---|---|---|
| 4,452,235 | 6/1984 | Reynolds . |
| 4,461,294 | 7/1984 | Baron . |
| 4,781,187 | 11/1988 | Herrick . |
| 5,425,727 | 6/1995 | Kozoil . |
| 5,722,971 | 3/1998 | Peyman . |

FOREIGN PATENT DOCUMENTS

| | | |
|---|---|---|
| 296153 | 11/1971 | (SU) . |
| 1066591 | 1/1984 | (SU) . |
| WO 95/03755 | 2/1995 | (WO) . |
| WO 96/40005 | 12/1996 | (WO) . |

OTHER PUBLICATIONS

Sawusch, M.R. and Mc Donnell, P.J., Computer Modeling of Wound Gape Following Radial Keratotomy, *Refractive & Corneal Surgery* 8:143–145 (1992).
Sawusch et al., Tissue Addition Theory of Radial Keratotomy: A Geometric Model, *Journal of Cataract Refractive Surgery* 17:448–453 (1991).
International Search Report of PCT/US98/05720.

*Primary Examiner*—David J. Isabella
(74) *Attorney, Agent, or Firm*—Klarquist Sparkman Campbell Leigh & Whinston, LLP

(57) ABSTRACT

A method, implant, and apparatus to alter the refractive power of the cornea. The method involves creation of radial, intrastromal corneal incisions and insertion of semirigid, biocompatible implants (13). An apparatus (26) is provided to facilitate creation of the incisions with precise depth, orientation, and dimension. The implants (13) are of predetermined shape and curvature in accordance with the patient's pre-existing refractive error and corneal curvature. The implants (13) induce a predictable and stable flattening or steepening of corneal curvature for the correction of refractive errors. If residual refractive error is present following this procedure, the curvature or dimensions of the implants may be selectively increased or decreased by application of laser or other energy source to a heat-shrinkable portion of the implants, thereby eliminating residual refractive error.

29 Claims, 3 Drawing Sheets

METHOD, IMPLANT, AND APPARATUS FOR REFRACTIVE KERATOPLASTY

This application claims the benefit of U.S. Provisional application Ser. No. 60/014,169 filed Mar. 26, 1996.

BACKGROUND OF THE INVENTION

The invention relates to a method, implant, and apparatus for altering the curvature of the cornea of the eye for the correction of refractive errors.

It is well known that refractive errors can be corrected by reshaping the cornea of the eye to obviate the need for glasses or contact lenses. Reshaping of the cornea may be accomplished in several ways. Prior art techniques of refractive surgery are discussed in detail in the text entitled "Refractive Keratotomy for Myopia and Astigmatism" by George O. Waring III published by Mosby Year Book of St. Louis, Mo., 1992. For example, the well known radial keratotomy method for correction of myopia involves the creation of multiple radial incisions through epithelium, Bowman's membrane, and at least 90% of the stromal thickness. This results in marked weakening of the structural integrity of the midperipheral cornea, causing relative steepening in this region and relative flattening of the central corneal curvature. This method has been associated with a number of undesirable factors including undercorrection or overcorrection of refractive error, fluctuating vision, corneal rupture from trauma, regression or progression of refractive effect, inability to correct high myopia, and infection of corneal incisions.

Another method of reshaping the cornea involves the use of lasers to ablate portions of the anterior surface to precise depths, as disclosed in U.S. Pat. No. 4,732,148. This method has also been associated with undercorrection or overcorrection of refractive errors, creation of haze or scarring within the visual axis, regression of refractive effect, a prolonged healing period, and requires use of expensive equipment. U.S. Pat. No. 4,461,294 describes the use of laser energy to vaporize light-absorbing pigments or dyes injected into the corneal stroma to produce multiple radial corneal scars. The corneal scars contract along their length resulting in flattening of central corneal curvature for the correction of myopia. However, variable wound healing following this procedure might result in unpredictable refractive effect.

Intracorneal synthetic or biological implants have been described in the prior art for alteration of corneal curvature. For example, U.S. Pat. No. 4,607,617 describes the implantation of synthetic lenses within the central corneal stroma for correction of refractive errors. These implants and methods have been associated with undesirable side effects including necrosis of tissue anterior to the implant due to interference with nutrient transfer, irreversible scarring and vascularization within the visual axis, undercorrection and overcorrection of refractive error, and the surgery can be technically difficult to perform.

U.S. Pat. No. 5,300,118 and related patents describe the implantation of a single intrastromal, circumferential, biocompatible ring of varied thickness for the correction of refractive errors. This implant exerts a direct conformational change upon the cornea resulting in flattening of the central cornea in proportion to the thickness of the ring. However, this prior art differs from the present invention in several ways, including 1) the present invention utilizes an implant of much smaller dimensions and of a completely different shape, 2) the implants of the present invention are placed radially within the cornea instead of circumferentially, 3) only the present invention allows adjustment of refractive effect by application of heat to the implants, 4) the radial placement of the implants of the present invention is technically easier to perform and is less error-prone than the circumferential placement of the prior art method, 5) the radial placement of the implants of the present invention exert different stress vectors on the cornea than the prior art, 6) the prior art uses one or two ring-shaped implants always placed in the same corneal location whereas the present invention uses 1 to 30 implants placed in a variety of locations, corneal depths, and distances from the central cornea depending on preexisting refractive error, 7) the prior art uses implants all of the same initial curvature whereas the present invention uses implants of various preselected curvatures, 8) the present invention allows more selective alteration of refractive effect by removing and replacing individual small implants which only affects the corneal curvature immediately surrounding the implant instead of large portions of the cornea with the prior art, and 9) the prior art method requires a very different and more complex apparatus to create the corneal incisions for the implant.

U.S. Pat. No. 4,781,187, a modification of the radial keratotomy procedure, describes the suturing of donor corneal tissue implants of rectangular or triangular geometry within conventional radial keratotomy incisions. This method provides variable change in corneal curvature by controlling the amount of gape within radial keratotomy incisions. The implants described in this patent are relatively nonrigid and do not directly exert conformational changes upon the surrounding cornea. These implants maintain the gaping of radial incisions at the corneal surface, thereby increasing the circumference of the mid-peripheral cornea. This prior art differs from the present invention in several ways including the requirement of deep corneal incisions extending to the outer surface of the cornea and is associated with undesirable factors such as difficulty of producing and handling very thin donor corneal implants of precise thickness, and overcorrections or undercorrections due to variable wound healing and variability of suture tightness. The wound healing variability associated with conventional radial keratotomy would also apply to this prior art procedure.

SUMMARY OF THE INVENTION

It is an object of the present invention to overcome the disadvantages associated with prior art techniques of correcting refractive error by modification of corneal curvature.

The present invention provides a means of modifying corneal curvature in a predictable, reversible, and adjustable fashion. The method involves insertion of semirigid, biocompatible implants into the midperipheral corneal stroma. The implants are of predetermined shape and curvature based upon the patient's refractive error and corneal curvature. The implants induce a predictable conformational change in corneal curvature, e.g. central flattening for correction of myopia or steepening for correction of hyperopia. If residual refractive error is present following the initial procedure, the dimensions or curvature of the implants may be altered by the application of heat by laser or other source to a heat-shrinkable portion of the implants. This provides selective enhancement or decrease of refractive effect and may be done at any time following the initial procedure.

It is an object of the invention to alter corneal curvature by inducing conformation of the less rigid cornea to the shape of more rigid implants placed within incisions in the corneal stroma. The creation of intrastromal incisions alone does not result in significant change in corneal curvature (see Sawusch MR, Computer Modeling of Wound Gape Following Radial Keratotomy, Refractive and Corneal Surgery, March/April 1992, p 143–5). The modification of corneal curvature is dependent upon the curvature, corneal location, dimensions, and stiffness or Young's modulus of the corneal implants.

It is another object of the invention to provide an apparatus for the creation of radial, intrastromal corneal incisions of defined depth, length, and diameter to facilitate insertion of the intrastromal implants.

Unlike radial keratotomy (and modifications such as U.S. Pat. No. 4,781,187), the present invention does not involve deep incisions through epithelium, Bowman's membrane, and large portions of corneal stroma in order to weaken the structural integrity of the cornea to cause change in shape. Thus, the present invention does not decrease the structural integrity of the cornea. In addition, intrastromal incisions are smaller and would be expected to heal faster and with less scarring and less variability than those required for radial keratotomy. Intrastromal incisions may also be less susceptible to late infection since the corneal epithelium and Bowman's membrane remains largely intact. Preliminary data also suggest that the present invention can effect larger changes in corneal curvature than are possible from radial keratotomy.

It is an object of the invention to alter central corneal curvature secondarily without surgically violating the "central optical zone," the central 3 mm of the corneal apex centered on the visual axis. Unlike excimer laser photorefractive keratectomy or intracorneal lenses, the present invention cannot result in vision-reducing scarring or haze within the central optical zone since this region is not operated upon. In the present invention, the central corneal curvature is altered secondarily by the implants present in the adjacent mid-peripheral cornea. For example, for correction of myopia, the major axis of the implants is relatively more curved than the native cornea and therefore causes a steepening of curvature of the mid-peripheral corneal curvature, which secondarily results in a flattening of the central corneal curvature to correct the refractive error.

It is an object of the invention to provide corneal implants for correction of refractive error which are of sufficiently small transverse diameter so that they do not interfere with nutrient transfer within the cornea and thereby avoid necrosis of corneal tissue.

It is an object of the invention to provide a simple and precise means to modify the effect of surgery at any time following the insertion of the implants. If the patient is left with residual refractive error following the initial procedure and wound healing, the curvature or dimensions of the intrastromal implants may be altered in-situ by the application of laser or other energy source to effect heat-shrinkage of portions of the implants. The laser or other heat source is focused or concentrated on the implant material and may be preferentially absorbed by dyes within the implant material. The adjacent transparent corneal tissue would not absorb the laser energy and therefore no scarring nor wound healing response would result.

It is an object of the invention to allow reversibility of corneal curvature change. If the curvature change is not appropriate or no longer desired, the corneal implants may be removed and the cornea will resume the original shape. The surgeon also has the option of replacing implants with those of a different curvature or dimensions if a different corneal curvature is desired.

These and other objects of the invention will be apparent to those skilled in the art, in light of the accompanying description, drawings and appended claims.

DESCRIPTION OF PREFERRED EMBODIMENTS

Before explaining the present invention in detail, it is to be understood that the invention is not limited in its application to the details of the construction and arrangement of parts illustrated in the accompanying diagrams. The invention is capable of other embodiments and of being practiced or carried out in a variety of ways. It is to be understood that the phraseology and terminology employed herein is for the purpose of description and not limitation.

Figure 1:
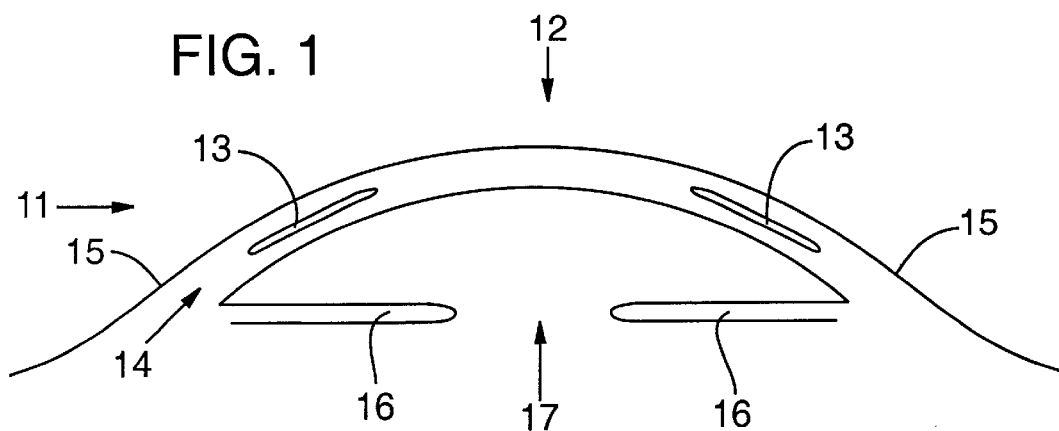
FIG. 1 is a cross-sectional view of the cornea containing intrastromal implants.

The invention is directed at correcting refractive errors of the human or animal eye, including myopia, hyperopia, and astigmatism, by altering the curvature of the cornea. Referring first to FIG. 1 of the drawings, a cross-section of the anterior portion of the human eye is shown with the cornea 11 representing the transparent, dome-shaped outer coating of the eye. The central optical zone 12 is the portion of the cornea which corresponds to the visual axis. In patients having myopia, the central corneal curvature is too steep and the light rays are focused in front of the retina; flattening of the cornea allows light rays to focus on the retina for clear vision. In patients having hyperopia, the central corneal curvature is too flat and the light rays are focused behind the retina; steepening of the cornea allows light rays to focus on the retina. Placement of semirigid radial implants 13 having selected curvature or dimensions within the corneal stroma 14 results in a predictable steepening or flattening of the central cornea to correct refractive errors. FIG. 1 also illustrates additional anatomic features of the eye including the peripheral aspect of the cornea called the limbus 15, the iris 16, and the pupil 17.

The surgeon must first determine the patient's refractive error and corneal curvature by conventional means, including use of a keratometer or corneal topography mapping device. Refraction, keratometry, and patient age variables are employed by a nomogram or computer program to select the curvature, dimensions, and number of implants, and locations within the cornea of each implant necessary to achieve a desired refractive effect. Locations within the cornea may be specified in three dimentions, i.e. the meridian in degrees, the relative corneal depth, and the proximity to the center of the cornea. Finite element modeling or empirical data may be used to assist in determining these variables for a given cornea.

Figure 2:
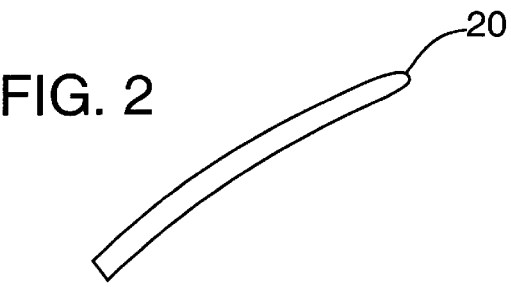
FIG. 2 is an isometric view of a suggested shape for an intrastromal implant.
Figure 3:
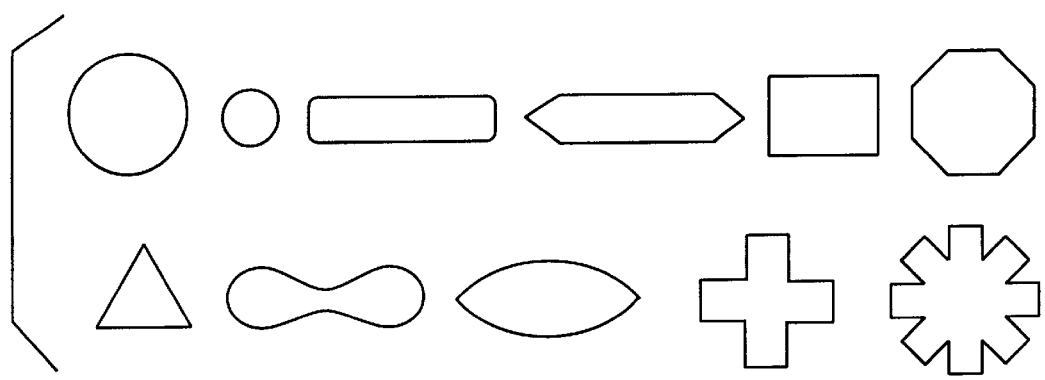
FIG. 3 illustrates transverse cross-sectional views of other potential implant shapes.

The corneal implant curvature and dimensions have been selected according to the nomogram or computer program as described above. FIG. 2 illustrates one embodiment of the shape of the corneal implants. The leading end or tip 20 of the implant may be rounded, flat, or tapered to facilitate dissection of tissue during insertion. FIG. 3 illustrates transverse cross-sectional views of other embodiments of the shape of the corneal implants. The cross-sectional dimentions may be held constant throughout the length of the implant or progressively diminished to allow a more pointed configuration. The implants are available in a variety of lengths, transverse shapes, and curvatures along the longitudinal axis to allow for the correction of a wide variety of refractive errors. For example, implants that have a greater curvature than a given cornea may result in central corneal flattening to correct myopia, whereas implants that have a lesser or inverse curvature than a given cornea may result in central corneal steepening to correct hyperopia. Implants which are longer or of wider transverse dimensions would also tend to produce a greater change in corneal curvature. Implants placed within one meridian may add cylindrical power if more curved than the cornea in that meridian or subtract cylindrical power if less curved than the cornea in that meridian. The implants may be fashioned from semi-rigid biocompatible materials including, but not limited to, polymethylmethacrylate (PMMA), Prolene (TM), Sauflon (TM), acrylic, nylon (TM), and other heat-shrinkable plastics. Dyes may be incorporated within the implant material to increase the absorption of light energy from a laser or other heat source. The dye may be present throughout the entire implant or limited to particular portions of the implant.

The procedure may be performed in the following fashion. The cornea is anesthetized with topical anesthetic drops. The optical center of the cornea is marked while the patient stares at a fixation light. An optical zone marker is centered over the optical center and radial keratotomy incision marker used to assist in orienting intrastromal incisions. These steps are identical to those prior to performing radial keratotomy and are described in detail in the above reference by Waring. A guarded surgical blade is placed at the peripheral aspect of each incision mark and used to make a small radial incision to a depth of approximately 400–500 microns or approximately one-half peripheral corneal thickness.

Figure 4A:
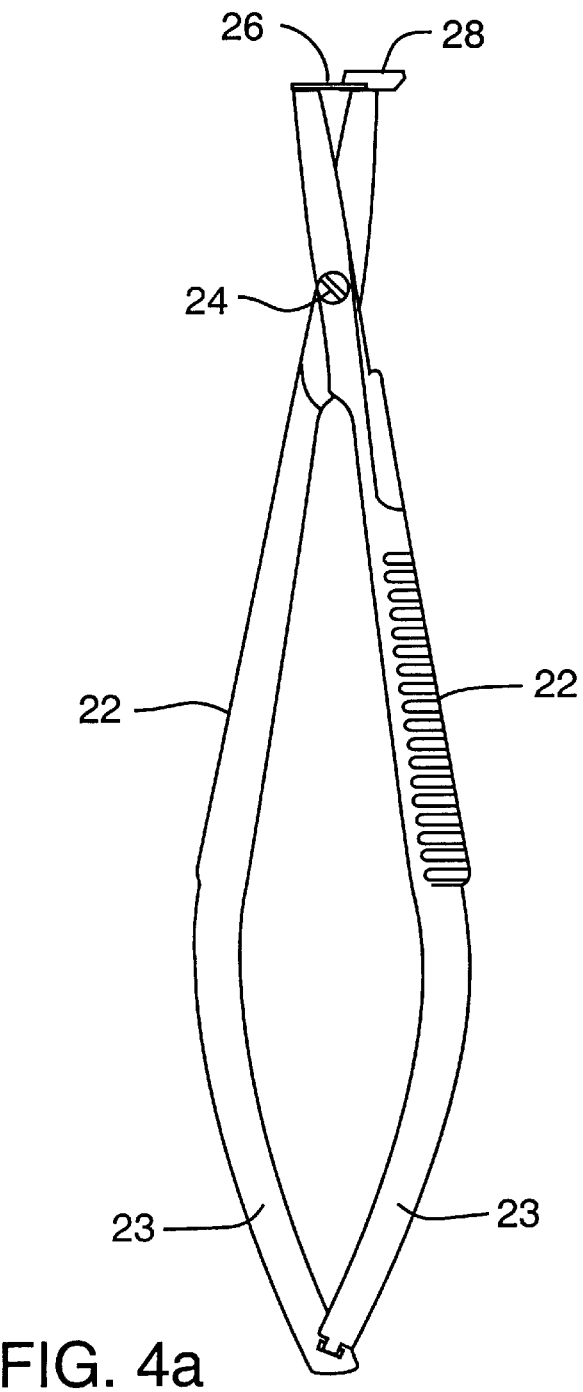
FIG. 4a is an isometric view of a hand-held surgical apparatus used to create radial intrastromal incisions to allow insertion of intrastromal implants.
Figure 4B:
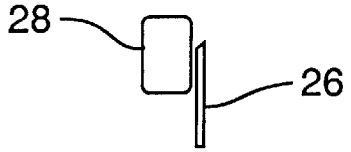
FIG. 4b is a forward end view of the apparatus used to create radial intrastromal incisions.

The apparatus shown in FIG. 4a may be used to create radial, intrastromal incisions of desired depth and dimension. The apparatus is preferrably formed from stainless steel or titanium. The apparatus consists of two handles 22 tapered and joined at one end by a spring 23. At the other end the handles are joined by a pivot 24 allowing the handles to be squeezed together. The extension of one of the handles beyond the pivot consists of an angled portion 26 that is narrow, elongated, and tapered to permit penetration and dissection of corneal tissue. The extension beyond the pivot of the other handle consists of a angled and widened member, the footplate 28, which may be placed on the corneal surface and used to maintain the position of the apparatus while the handles are squeezed together. The stromal dissector 26 is displaced from the footplate 28 at the desired depth for the corneal implants below the corneal surface. This device is placed with the footplate 28 adjacent to the previously made peripheral corneal incision and oriented in alignment with the radial incision mark. The spring handles 22 are then squeezed by the surgeon to dissect within the corneal lamellae and create a radial intrastromal incision with a diameter the same as that of the stromal dissector 26. Once the stromal dissector 26 has reached the optical zone mark, the pressure on the spring handles 22 is released to allow the spring handles 23 to remove the stromal dissector 26 from the cornea. This process is repeated in other corneal meridians to create the desired number of intrastromal incisions called for by the nomogram or computer program. Alternatively, the surgeon may use a freehand hypodermic or solid needle or thin blade to create the radial intrastromal incisions. Alternatively, the corneal implant may be injected into virgin corneal tissue to create an incision simultaneous with placement of the implant. With each of these methods, the intrastromal incisions remain within the corneal stroma throughout their length and do not violate Bowman's membrane or epithelium anteriorly (except at the initial entry point of the incision) nor violate Descemet's membrane posteriorly.

Figure 5A:
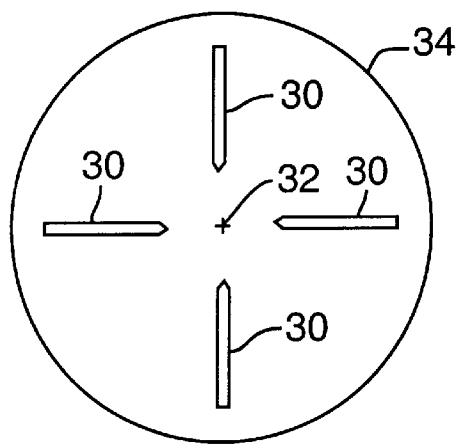
FIG. 5a is an anterior or top view of a cornea containing intrastromal implants in a symmetric pattern of locations.
Figure 5B:
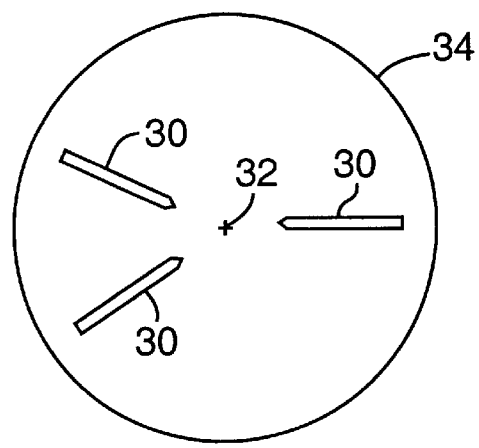
FIG. 5b is an anterior or top view of a cornea containing intrastromal implants in an asymmetric pattern of locations.

The corneal implant curvature and dimension have been selected according to the nomogram or computer program as described above. The surgeon then inserts or injects the corneal implant into the intrastromal incision all the way to the optical zone mark. It may be necessary to push down on the cornea just anterior to the implant as it is inserted to assist in free passage. The entire implant will rest within the incision such that no portion is exposed. If necessary, a suture may be used to close the initial peripheral incision if gaping occurs. This process is repeated until the desired number of implants have been placed. FIG. 5a illustrates an anterior or top view of a cornea containing four radial stromal implants 30. Note that the implants are present within the midperipheral cornea and do not enter the central optical zone or "visual axis," the area immediately surrounding the center of the cornea or corneal apex 32. Note placement of the implants radially with respect to the corneal apex 32 and the corneal periphery or limbus 34. Although this Figure illustrates a symmetric placement of implants, an asymmetric placement may be indicated for correction of astigmatism. One example of this is shown in FIG. 5b. In addition, the number of implants to be used may range between 1 to 30, depending upon the type and degree of refractive error to be corrected.

Postoperatively, if residual refractive error is present and it is desirable to correct it, a laser or other heat source can be focused or directed upon the implants within the corneal stroma to effect a change in the implant curvature or dimensions due to heat-shrinkage of the implant material. A suitable laser source would be a typical ophthalmic Argon laser which can be focused to a 50–100 um spot size and applied accurately to a small portion of the intrastromal implant material. The 488 nm or 514nm wavelength of the Argon laser is not absorbed by transparent corneal tissue, but can be selectively absorbed by dyes within the implant material. The amount of change of the curvature or dimensions may be precisely controlled by altering the number of laser applications, the location of laser applications, dye concentration or composition within the implant, the energy per application, the laser spot size, and the laser wavelength. The curvature or length change desired for each intrastromal implant can be determined based upon the corneal curvature immediately surrounding each implant, as can be determined by computerized corneal topography or keratometry. Since heat-shrinkage of the implant material is likely to reduce the conformational change exerted by the implant, it may be desirable to select an initial implant curvature or dimensions which are likely to over-correct the refractive error and then use the laser to accurately reduce the over-correction until the corneal curvature provides the desired refractive error or emmetropia.

Should the implants ever require removal, such as due to selection of incorrect implant dimensions or curvature, a small radial incision may be made in the corneal periphery over the implant material in the same fashion as described above. The implant material may then be withdrawn with a forceps and the intrastromal incision left empty or a new implant placed within the incision as described above. If the implant material is removed and not replaced, it is expected that the corneal shape and refractive change will be reversible and return to the preoperative state.

Figure 6:
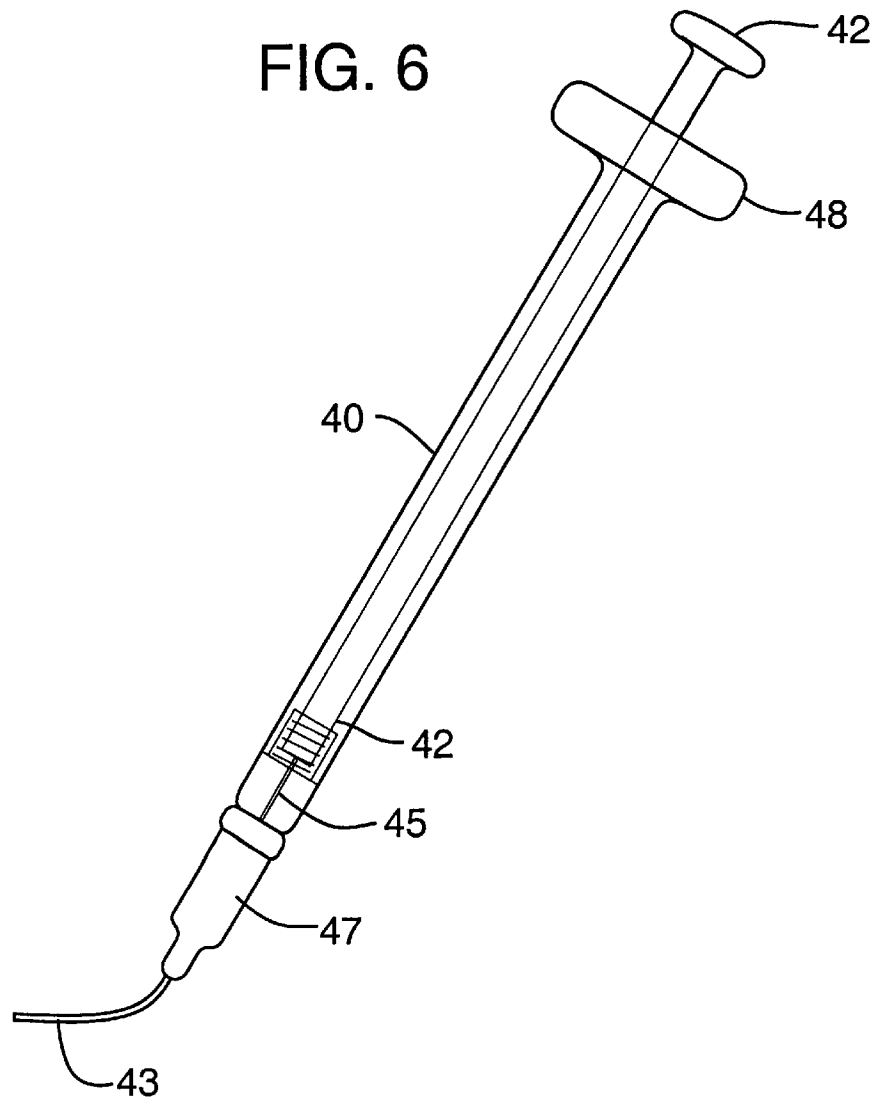
FIG. 6 is an isometric view of another embodiment of the surgical apparatus used to insert corneal implants.

FIG. 6 illustrates a second embodiment of the apparatus used to facilitate insertion of the intrastromal implants. This embodiment permits simultaneous creation of intrastromal incisions and insertion of intrastromal implants. The apparatus consists of an adapted hypodermic syringe with a narrow tube 40 fitted at one end with a piston 42 and at the other end with a hollow needle 43 and hub assembly 47. An advancing wire 45 extends between the piston 42 and the needle 43. The corneal implant is placed entirely within the bore of the needle 43 between the forward cutting end of the needle and the forward end of the advancing wire 45. This apparatus does not require creation of a separate initial peripheral radial incision. The needle 43 may be curved to facilitate orientation of the needle in the radial direction from corneal periphery to the corneal apex while the syringe 40 is held approximately perpendicular to the corneal limbus. The implant material is preloaded into the bore of the needle in the proper orientation, e.g. curvature up or down. Corneal optical zone markers are used to create marks at the entrance site of the needle in the corneal periphery and at the central optical zone. Radial marks may be made with a conventional radial keratotomy corneal marker to connect the peripheral and central marks. The apparatus is placed with a portion of the needle 43 firmly in contact with the peripheral cornea, limbus, and sclera. The needle 43 is also oriented radially with respect to the center of the cornea and such that the tip enters the cornea at the peripheral corneal mark. The forward cutting end of the needle 43 is then advanced toward the central cornea by the surgeon until reaching the central optical zone mark. The portion of the needle 43 that has not yet entered the corneal stroma remains in contact with the surface of the cornea, limbus, and sclera while the needle 43 is advanced. This serves to stabilize and orient the needle so that it travels within the corneal stroma. The advancing wire 45 is then advanced into the bore of the needle 43 by pushing on the piston 42 in order to push the implant material out of the needle 43 and into the corneal stroma. Advancement of the piston is facilitated by countertraction on the syringe flange 48. Simultaneously, the surgeon removes the needle 43 from the corneal stroma while the implant material is advanced into the stroma, thereby allowing the implant to occupy the potential space created by the needle 43. This allows placement of the implant material within the corneal stroma while minimizing disturbance of surrounding tissue. Alternatively, the implant may be fashioned with a sharpened tip to permit dissection of corneal stroma by advancement of the implant rather than by the needle 43.

While particular embodiments of the invention have been shown and described, it will be obvious to those skilled in the art that changes and modifications may be made without departing from the invention in its broader aspects.

I claim:

1. A method of altering a curvature of a cornea to correct a refractive error, comprising:

making an initial incision through a corneal epithelium or limbus;

introducing an intrastromal implant radially into the cornea through the initial incision and advancing the implant through a corneal stroma without entering a central optical zone, the implant being shaped to substantially correct the refractive error.

2. The method of claim 1, wherein the implant is an elongated member having a long axis which is advanced advanced radially into the corneal stroma, below a corneal epithelium and Bowman's membrane, through the initial incision in the corneal epithelium or limbus, through which initial incision the long axis of the implant is introduced.

3. The method of claim 2, wherein after introduction through the initial incision, the implant is introduced radially into the incision without interrupting Bowman's membrane, and without entering a central optical zone of the cornea.

4. The method of claim 3, wherein the implant is capable of changing its curvature or other dimension in response to radiant energy, and the method further comprises altering the curvature or other dimension of the implant by applying radiant energy to the implant in situ, to which the implant responds by changing its curvature or other dimension.

5. The method of claim 4, wherein the radiant energy is from a laser source.

6. The method of claim 4, wherein the implant comprises a material that changes in response to the radiant energy, but the radiant energy is not substantially absorbed by the cornea and does not substantially alter the cornea.

7. The method of claim 1, wherein the implant is placed in a subject having myopia, and the implant has a curvature greater than the corneal curvature prior to introduction of the implant, to flatten a central curvature of the cornea.

8. The method of claim 1, wherein the implant is placed in a subject having hyperopia, and the implant has a curvature less than the corneal curvature prior to introduction of the implant, to steepen a central curvature of the cornea.

9. The method of claim 1, wherein introducing a stromal implant comprises inserting a plurality of implants into the cornea.

10. The method of claim 9, wherein inserting the plurality of implants comprises radially inserting the plurality of the implants substantially symmetrically about the cornea.

11. The method of claim 9, wherein inserting the plurality of the implants comprises radially inserting the plurality of radial implants asymmetrically about the cornea.

12. The method of claim 11, wherein the plurality of radial implants are introduced asymmetrically into the cornea of a subject having astigmatism.

13. The method of claim 6, wherein the radiant energy is from a laser, and the material that changes in response to the radiant energy comprises a dye associated with the implant that absorbs energy of a wavelength of the laser light that is used, to heat the implant where the radiant energy is absorbed, and the wavelength of the laser is substantially not absorbed by the cornea.

14. The method of claim 6, wherein the laser source is an Argon laser.

15. The method of claim 1, further comprising inserting a plurality of the implants radially in the cornea to achieve a desired refractive correction.

16. The method of claim 9, further comprising selectively removing at least one of the implants after they have been introduced into the cornea.

17. The method of claim 2 wherein the implant is elongated, and the method further comprises making a radial tunnel in the cornea below the corneal epithelium, through the initial incision, prior to introducing the implant into the cornea.

18. The method of claim 2, wherein the implant is elongated and forms an incision in the cornea as the implant is introduced into the cornea.

19. The method of claim 1, wherein the implant is substantially linear in shape.

20. The method of claim 1, wherein the implant has a tapered leading end that facilitates introduction of the implant into the cornea, and the implant is introduced tapered end first into the cornea.

21. The method of claim 1, wherein the implant comprises at least a portion made of heat-shrinkable plastic.

22. A method of altering a curvature of a cornea to correct a refractive error in a subject, comprising:

providing an elongated implant, wherein the implant has a preselected curvature or shape, along its longitudinal axis, designed to offset a refractive error in a subject;

making an initial incision in a periphery or limbus of the cornea;

inserting the implant into a stroma of the cornea through the initial incision, without entering a central optical zone or disrupting the epithelium at other than the initial incision, wherein a greatest width of the implant substantially conforms to the dimensions of the initial incision as the implant is introduced along its longitudinal axis radially into the cornea.

23. The method of claim 22, wherein the implant comprises a heat shrinkable material, and the method further comprises heating the heat shrinkable material of the implant after introduction of the implant into the cornea to change a curvature of the implant.

24. The method of claim 23, wherein the heat shrinkable material comprises a dye introduced into the implant to absorb laser energy of a preselected wavelength, which laser energy is substantially not absorbed by the cornea, and heating the heat shrinkable material comprises directing the laser energy at a portion of the implant which contains the dye.

25. The method of claim 2, further comprising injecting the implant into the corneal stroma.

26. The method of claim 2, wherein the implant comprises a tapered leading edge which facilitates insertion of the implant into the cornea, the elongated implant is curved along a longitudinal axis that is designed to extend radially in the cornea, the implant is not curved transversely, and the implant is substantially uniform in width along its length, and comprises a dye that absorbs radiant energy to change a curvature or other dimension of the implant.

27. The method of claim 22, further comprising forming a stromal tunnel below the epithelium from the initial incision prior to introducing the implant into the cornea.

28. The method of claim 27, wherein forming a stromal tunnel comprises introducing a penetrating member into the cornea.

29. The method of claim 28, wherein introducing a penetrating member comprises providing an instrument comprising first and second pivotal arms, wherein one arm comprises a support member to rest on the cornea, and the other arm carries the penetrating member, and resting the support member on the cornea and pivoting the first and second pivotal arms toward eachother, such that the penetrating member forms the initial incision and the stromal tunnel into which the implant is introduced.

* * * * *